US010519324B2

(12) United States Patent
Mount et al.

(10) Patent No.: US 10,519,324 B2
(45) Date of Patent: Dec. 31, 2019

(54) CONOTOXIN PEPTIDES FOR USE IN BIOFOULING DETERRENCE

(71) Applicant: Clemson University Research Foundation, Clemson, SC (US)

(72) Inventors: Andrew S. Mount, Mountain Rest, SC (US); Bin San Chan, Hong Kong, CA (US); Mary Beth Johnstone, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 10 days.

(21) Appl. No.: 15/576,522

(22) PCT Filed: May 19, 2016

(86) PCT No.: PCT/US2016/033275
§ 371 (c)(1),
(2) Date: Nov. 22, 2017

(87) PCT Pub. No.: WO2016/191200
PCT Pub. Date: Dec. 1, 2016

(65) Prior Publication Data
US 2018/0155554 A1    Jun. 7, 2018

Related U.S. Application Data

(60) Provisional application No. 62/165,345, filed on May 22, 2015.

(51) Int. Cl.
*C09D 5/16*    (2006.01)
*C07K 7/08*    (2006.01)
*C07K 14/435*    (2006.01)

(52) U.S. Cl.
CPC .............. *C09D 5/1625* (2013.01); *C07K 7/08* (2013.01); *C07K 14/43504* (2013.01); *C02F 2303/20* (2013.01)

(58) Field of Classification Search
CPC ................................ C09D 5/1625; C07K 7/08
See application file for complete search history.

(56) References Cited

U.S. PATENT DOCUMENTS

| | | | |
|---|---|---|---|
| 7,851,444 B2 | 12/2010 | Lewis et al. | |
| 9,371,451 B2 | 6/2016 | Mount et al. | |
| 9,560,848 B2 | 2/2017 | Mount et al. | |
| 2003/0170222 A1* | 9/2003 | Jones ............... | C07K 14/43504 424/94.1 |
| 2004/0176278 A1* | 9/2004 | Jones ............... | C07K 14/43504 424/1.69 |
| 2005/0143560 A1* | 6/2005 | McIntosh ......... | C07K 14/43504 530/327 |
| 2005/0271589 A1* | 12/2005 | Jones ............... | C07K 14/43504 424/1.69 |
| 2009/0005316 A1* | 1/2009 | McIntosh ......... | C07K 14/43504 514/21.4 |
| 2012/0122803 A1* | 5/2012 | McIntosh ......... | C07K 14/43504 514/21.4 |
| 2012/0285829 A1 | 11/2012 | Mount et al. | |
| 2012/0329717 A1* | 12/2012 | Lewis .............. | C07K 14/43504 514/15.7 |
| 2016/0348150 A1 | 12/2016 | Bachmann et al. | |

FOREIGN PATENT DOCUMENTS

| | | |
|---|---|---|
| WO | WO 1998/031705 | 7/1998 |
| WO | WO 1998/31705 A1 | 7/1998 |
| WO | WO 2000/020444 | 4/2000 |
| WO | WO 2000/20444 B2 | 4/2000 |
| WO | WO 2003/081199 | 10/2003 |
| WO | WO 2003/081199 A1 | 10/2003 |
| WO | WO 2009/134303 A2 | 11/2009 |
| WO | WO 2009/135258 | 11/2009 |

OTHER PUBLICATIONS

EPO Extended Search Report, dated Oct. 26, 2018.
International Search Report, dated Sep. 26, 2016, 3 pages.
Aldred, et al. Confocal microscopy-based goniometry of barnacle cyprid permanent adhesive. *The Journal of Experimental Biology.* 216; (2013), pp. 1969-1972.
Frost & Sullivan. Strategic Analysis of the Global Market for Marine Coatings. (2012).
Gohad, et al. Observations on the settlement and cementation of barnacle (*Balanus amphitrite*) cyprid larvae after artificial exposure to noradrenaline and the locations of adrenergic-like receptors. Journal of Experimental *Marine Biology and Ecology* 416, (2012), pp. 153-161.
Gohad, et al. Noradrenaline deters marine invertebrate biofouling when covalently bound in polymeric coatings. *Journal of Experimental Marine Biology and Ecology* 394(1), (2010), pp. 63-73.
Heath-Heckman, et al. The occurrence of chitin in the hemocytes of invertebrates. *Zoology* 114, (2011) pp. 191-198.
Imbesi, et al. Noradrenaline-Functionalized Hyperbranched Fluoropolymer—Poly (ethylene glycol) Cross-Linked Networks As Dual-Mode, Anti-Biofouling Coatings. *ACS Nano* 6(2), (2012), pp. 1503-1512.
Lewis R. Discovery and development of the χ-conopeptide class of analgesic peptides. *Toxicon* 59, (2012), pp. 524-528.
Markets and Markets. Marine Coatings Market by Resin (Epoxy, Alkyd, Polyurethane, Acrylic, Polyester, and Fluoropolymer), Product Type (Anti-corrosion Coating, Antifouling Coating), Applications (Cargo Ship, Passenger Ship, Boat), and Region—Global Forecast to 2022. (2018). http://www.marketsandmarkets.com/Market-Reports/marine-coatings-market-234885004.html.
Maruzzo, et al. Metamorphosis in the cirripede crustacean *Balanus amphitrite*. *Plos One.* 7(5), (2012), pp. 1-8.
Skala, et al. In vivo multiphoton microscopy of NADH and FAD redox states, fluorescence lifetimes and cellular morphology in precancerous epithelia. *PNAS* 104(49), (2007), pp. 19494-19499.
Zhang, et al. The oyster genome reveals stress adaptation and complexity of shell formation. *Nature* 490, (2012), pp. 49-54.

\* cited by examiner

*Primary Examiner* — Amber D Steele
(74) *Attorney, Agent, or Firm* — Dority & Manning, P.A.

(57) ABSTRACT

Materials and methods for prevention of biofouling are described that incorporate the presence of a conotoxin peptide on a surface. The conotoxin peptide is either directly or indirectly adhered to the surface and interferes with the ability of biofouling organisms to settle on the surface.

17 Claims, 1 Drawing Sheet
Specification includes a Sequence Listing.

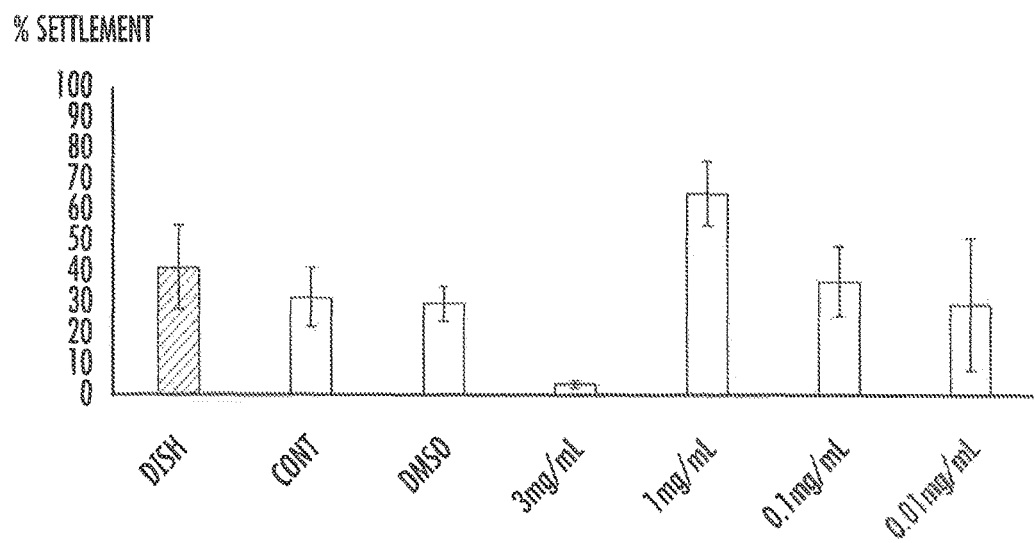

SEQUENCE LISTING

```
<160> NUMBER OF SEQ ID NOS: 14

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: 4-hydroxy proline

<400> SEQUENCE: 1

Asn Gly Val Cys Cys Gly Tyr Lys Leu Cys His Pro Cys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: 4-hydroxy proline

<400> SEQUENCE: 2

Val Gly Val Cys Cys Gly Tyr Lys Leu Cys His Pro Cys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MISC_FEATURE
<222> LOCATION: (2)..(2)
<223> OTHER INFORMATION: May or may not be present
```

```
<400> SEQUENCE: 3

Glu Asn Gly Val Cys Cys Gly Tyr Lys Leu Cys His Pro Cys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (12)..(12)
<223> OTHER INFORMATION: 4-hydroxy proline
<220> FEATURE:
<223> OTHER INFORMATION: C-term NH2

<400> SEQUENCE: 4

Glu Gly Val Cys Cys Gly Tyr Lys Leu Cys His Pro Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (12)..(12)
<223> OTHER INFORMATION: 4-hydroxyproline

<400> SEQUENCE: 5

Glu Gly Val Cys Cys Gly Tyr Lys Leu Cys His Pro Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (12)..(12)
<223> OTHER INFORMATION: 4-hydroxyproline
<220> FEATURE:
<221> NAME/KEY: MOD_RES
<222> LOCATION: (13)..(13)
<223> OTHER INFORMATION: D-cysteine

<400> SEQUENCE: 6

Glu Gly Val Cys Cys Gly Tyr Lys Leu Cys His Pro Cys
1               5                   10
```

```
<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (7)..(7)
<223> OTHER INFORMATION: 4-methoxy tyrosine
<220> FEATURE:
<221> NAME/KEY: MOD_RES
<222> LOCATION: (12)..(12)
<223> OTHER INFORMATION: 4-hydroxyproline

<400> SEQUENCE: 7

Glu Gly Val Cys Cys Gly Tyr Lys Leu Cys His Pro Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (8)..(8)
<223> OTHER INFORMATION: 4-methoxy tyrosine
<220> FEATURE:
<221> NAME/KEY: MOD_RES
<222> LOCATION: (13)..(13)
<223> OTHER INFORMATION: 4-hydroxyproline

<400> SEQUENCE: 8

Glu Asn Gly Val Cys Cys Gly Tyr Lys Leu Cys His Pro Cys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (13)..(13)
<223> OTHER INFORMATION: 4-hydroxyproline

<400> SEQUENCE: 9

Glu Asn Gly Val Cys Cys Gly Tyr Lys Leu Cys His Pro Cys
1               5                   10

<210> SEQ ID NO 10
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (12)..(12)
<223> OTHER INFORMATION: 4-hydroxyproline
<220> FEATURE:
<223> OTHER INFORMATION: Free acid C terminal

<400> SEQUENCE: 10

Glu Gly Val Cys Cys Gly Tyr Lys Leu Cys His Pro Cys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (12)..(12)
<223> OTHER INFORMATION: 4-hydroxyproline
<220> FEATURE:
<223> OTHER INFORMATION: Free acid C terminal

<400> SEQUENCE: 11

Glu Gly Val Cys Cys Gly Tyr Lys Leu Cys His Pro Cys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate or D-pyroglutamate
<220> FEATURE:
<221> NAME/KEY: MOD_RES
<222> LOCATION: (12)..(12)
<223> OTHER INFORMATION: 4-hydroxyproline

<400> SEQUENCE: 12

Glu Gly Val Cys Cys Gly Tyr Lys Leu Cys His Pro Cys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate
```

-continued

```
<220> FEATURE:
<221> NAME/KEY: MOD_RES
<222> LOCATION: (12)..(12)
<223> OTHER INFORMATION: 4-hydroxy proline
<220> FEATURE:
<223> OTHER INFORMATION: C-term NH2

<400> SEQUENCE: 13

Glu Gly Val Cys Cys Gly Tyr Lys Leu Cys His Pro Cys
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term COOH
<220> FEATURE:
<223> OTHER INFORMATION: C-term modified by a functional group capable
      of binding to a substrate surface

<400> SEQUENCE: 14

Gly Gly Gly Gly Gly Gly Gly
1               5
```

CONOTOXIN PEPTIDES FOR USE IN BIOFOULING DETERRENCE

CROSS REFERENCE TO RELATED APPLICATION

This application claims filing benefit of U.S. Provisional Patent Application Ser. No. 62/165,345 having a filing date of May 22, 2015, which is incorporated by reference herein in its entirety.

STATEMENT AS TO INVENTIONS MADE UNDER FEDERALLY SPONSORED RESEARCH

This invention was made with government support under grant no. N00014-14-1-0488 awarded by the Office of Naval Research (NAVY/ONR). The government has certain rights in the invention.

BACKGROUND

Biofouling is the undesirable accumulation of organisms including bacteria, plants, algae, and animals on submerged structures. Biofouling includes both microfouling (biofilm formation and bacterial adhesion) and macrofouling (attachment of larger organisms). Biofouling organisms are classified as hard or soft fouling types. Hard (calcareous) fouling organisms include barnacles, encrusting bryozoans, mollusks such as oysters, polycheate and other tube worms, zebra mussels and tunicates. For instance, the fully grown barnacle is a stationary calcareous arthropod characterized by a cone shell enclosing layers of calcinous plates. The mechanical strength of the barnacle's attachment is very high, and it is difficult to mechanically remove them from marine surfaces. Soft (non-calcareous) fouling organisms include seaweed, hydroids, algae and biofilm "slime". Successful removal of soft fouling organisms from marine surfaces also presents many difficulties.

Biofouling on aquatic vessels poses significant operational and safety issues. In some instances, the hull structure and propulsion systems can be damaged. Over time, the accumulation of biofouling materials on hulls can increase both the hydrodynamic volume of a vessel and the frictional effects leading to an increased drag, estimated to be up to 60% increase for a biofouled surface. The drag increase has been seen to decrease speeds by up to 10%, which can lead to increased fuel consumption. With fuel typically comprising up to half of aquatic transport costs, improved antifouling methods and materials could save the shipping industry billions of dollars each year. For example, the control of biofouling accumulation has become the single most expensive maintenance problem incurred by the U.S. Navy for ship operations.

Aquatic vessels are not the only surfaces subject to biofouling. Since biofouling can occur almost anywhere water is present biofouling poses risks to a wide variety of both fresh and saltwater submersible structures and presents significant cost issues to entire industries including paper manufacturing, food processing (aquaculture), underwater construction, oil and gas recovery, and desalination.

Historically, aquatic coatings (e.g., marine paints) have included biocides designed to leach from the coating over time to thereby prevent biofouling by virtue of the biocide's toxicity to biofouling organisms. Commonly used biocides have included certain metals and their salts. Two particular compounds, tributyltin (TBT) and cuprous oxide have been in commercial use for decades as antifouling agents in marine paints. However, TBT is now banned worldwide due to high toxicity of the leachate to free-floating organisms. Cuprous oxide is also of concern because of the build-up of leached copper in harbor sediment. Furthermore, broad spectrum leached biocides cannot be used in the aquaculture industry at all, as this industry requires agents that will not adversely affect the growth of the farmed fish themselves and which do not provide danger to the ultimate consumer.

Unfortunately, attempts to replace the traditional biocides with alternatives that are non-toxic when released into the surrounding water, or mechanical alternatives that could dislodge attaching marine growths, have met with limited success. For instance, self-polishing polymer coatings such as silicones and fluoropolymers (e.g., Teflon™) have offered possible alternatives to marine paints containing toxic antifouling agents. These coatings can have a low surface energy leading to low attachment capability of marine organisms. Unfortunately, however, these materials still require some sort of biocide additive to successfully prevent biofouling and hydrodynamic pressure still needs to be applied to dislodge the biofouling organism, i.e., merely the low surface energy surface is not enough to prevent biofouling.

Non-toxic surface-bound alternatives to leaching biocides have also been examined. For instance, it has been found that noradrenaline, a catecholamine with biological roles including as a hormone and a neurotransmitter, deters fouling marine invertebrates from settling when covalently bound to a surface or included as part of a coating which coats and covers a surface, thus preventing biofouling. Despite its antifouling effectiveness in lab studies, natural noradrenaline is not an ideal molecule for inclusion as an active agent in marine antifouling paints due to the fact that it has a short half-life (minutes) and it spontaneously oxidizes into adrenochrome, thus resulting in a loss of biological activity.

What are needed in the art are antifouling compounds that can be incorporated into coatings or otherwise applied on aquatic surfaces that can afford maximum protection from biofouling without harming the local environment.

SUMMARY

According to one embodiment, disclosed is a coating composition (e.g., a marine paint) that includes a conotoxin peptide.

Also disclosed are aquatic surfaces that include a conotoxin peptide directly or indirectly adhered thereto. For instance, in one embodiment, an aquatic surface, i.e., a surface intended for use in a freshwater or saltwater environment, can include a conotoxin peptide directly bonded thereto. In another embodiment, a surface can include a conotoxin peptide indirectly adhered thereto. For instance, the conotoxin peptide can be a component of an aquatic coating and can be blended with other components of the coating or can be bonded to another component of the coating composition. A surface can include the conotoxin peptide in a sufficient amount so as to prevent biofouling by an organism, for example, the surface can include the conotoxin peptide in an amount of about $10^{14}$ peptides per square centimeter of surface or greater as determined by an indirect density determination method.

According to another embodiment, disclosed is a method for preventing biofouling that includes adhering a conotoxin peptide to an aquatic surface.

BRIEF DESCRIPTION OF THE DRAWING

The present application may be better understood with reference to FIG. 1, which illustrates the settlement level of 3 day old cyprid on a surface held in a solution of χ-conotoxin at various solubilized concentration levels.

DETAILED DESCRIPTION

It is to be understood by one of ordinary skill in the art that the present discussion is a description of exemplary embodiments only, and is not intended as limiting the broader aspects of the present invention.

In general, disclosed herein are materials and methods for prevention of biofouling of an aquatic surface. More specifically, according to the present disclosure, one or more conotoxin peptides can be directly or indirectly adhered to an aquatic surface. The presence of the conotoxin peptide at the surface can prevent biofouling of the aquatic surface.

The term "aquatic surface" as used herein refers to any surface for use in or continuously or periodically exposed to either or both of sea water and freshwater in a natural environment such as an ocean, sea, lake, pond, or river, or in any other environment in which biofouling can occur. An aquatic surface can include, for instance, the lining of a pipe (e.g., water or sewer pipes), the inner surface of a tank, or any other surface that is constantly or periodically exposed to water and through that exposure can be subject to biofouling. Aquatic surfaces encompassed herein include, without limitation, surfaces of commercial and military ships (for both salt and fresh water) such as hulls, propellers, etc., fixed and floating marine structures such as offshore oil rigs, and recreational boats and yachts. Particular examples can include, for instance, military vessels, passenger ships, freighters, tankers, container ships, fishing boats and ferries, as well as oil rigs, inland waterway ships, barges, and tow boats. Aquatic surfaces can also encompass surfaces of docks, aqua culture equipment, power and desalination plant water intake and outflow systems, heat exchangers, grids, fish nets, fish cages, lines, biomedical surfaces (e.g., stents and other implantable devices), etc. Other surfaces susceptible biofouling and encompassed herein can include, for example, walls exposed to rain water, stock watering tanks, shower walls, roofs, gutters, pool areas, saunas, floors and walls exposed to damp environs such as basements or garages and the housing of tools and outdoor furniture.

Disclosed materials and methods can be utilized to prevent biofouling by marine and/or freshwater organisms capable of attaching to and colonizing submerged surfaces including, and without limitation, parazoans; coelenterates such as polychaete and oligochaete worms; mollusks; arthropods including crustaceans such as, but not limited to, acorn and goose barnacles; calcifying tubeworms; bryozoans; and sea tunicates, and to be effective in inhibiting the attachment and or development of the adult or larval forms of the targeted organisms. The antifouling compounds can also be effective against marine and freshwater plants including diatoms, algae and higher plants that can attach to a submerged surface. Disclosed compounds can also inhibit or otherwise effectively reduce the formation of biofilms to which colonizing organisms may attach.

Conotoxins are toxic peptides of marine snails of the genus *Conus* (cone snails). Cone snails are predators of fish, worms and other mollusks. They inject their prey with venom containing a cocktail of small bioactive peptides commonly referred to as conotoxins. Upon injection, the conotoxins interfere with neurotransmission by targeting a variety of receptors and ion-channels. The conotoxins are divided into classes on the basis of their physiological targets. The ω-conotoxin class of peptides target and block voltage-sensitive $Ca^{2+}$-channels inhibiting neurotransmitter release. The α-conotoxins and φ-conotoxins target and block nicotinic acetylcholine receptors, causing ganglionic and neuromuscular blockade. Peptides of the μ-conotoxin class act to block voltage-sensitive $Na^+$-channels inhibiting muscle and nerve action potentials. The δ-conotoxins target and delay the inactivation of voltage-sensitive $Na^+$-channels, enhancing neuronal excitability. The κ-conotoxin class of peptides target and block voltage-sensitive $K^+$-channels, and these also cause enhanced neuronal excitability. Conotoxins of the conopressin class are vasopressin receptor antagonists and those of the conantokin class are NMDA receptor antagonists. The γ-conotoxin class targets a voltage-sensitive nonspecific cation channel. The σ-conotoxin class antagonizes the $5HT_3$ receptor and the χ-conotoxin class inhibits neuronal amine transporters.

Without wishing to be bound to any particular theory, it is believed that the surface presence of a conotoxin peptide can prevent biofouling through interference of the settling and/or cementation processes of the biofouling organism and specifically through binding of the conotoxin peptides to cell surface receptors of the organisms. For instance, a surface can include one or more conotoxin peptides in an amount of about $10^{14}$ peptides per square centimeter of surface areas ($cm^2$) or greater, about $1.3 \times 10^{14}$ peptides/$cm^2$ or greater, or about $1.5 \times 10^{14}$ peptides/$cm^2$ or greater in one embodiment. The peptide surface density can be determined by an indirect method, i.e., utilizing the total weight of the peptide adhered to the surface, the number average molecular weight of the peptide, and the surface area covered by the peptide to arrive at the number of peptide molecules per square centimeter of coverage space.

Macroscopic settling organisms such as barnacles undergo development stages as free-swimming larvae, where the last larval stage is referred to as the cyprid stage. The cyprid screens solid surfaces suitable for settling with the help of a nervous protuberance, the antennule. A "settling-glue" referred to as balanus cement is secreted from specialized glands localized near the protuberance and the animal thereby settles to the solid surface. After settlement the animal undergoes a metamorphosis into an adult and stationary animal.

As previously mentioned, the biomolecule noradrenaline has previously been found to exhibit antifouling action when adhered to a surface. This antifouling action has been found to be through binding of the surface bound noradrenaline ligand to adrenergic receptors found in the neuronal cells of the sensory organs of macro-fouling marine invertebrate larvae. Once the noradrenaline ligand is bound to the adrenergic receptor, the animal's cells undergo apoptosis (programmed cell death) and marine larvae such as barnacle cyprids are inhibited from settling on treated surfaces.

The presence of conotoxin peptides on an aquatic surface are believed to function in a similar fashion in that they are believed to interfere with events necessary for settling of biofouling organisms. For instance, the presence of one or more of the conotoxin peptides on an aquatic surface is believed to bind adrenergic receptors in the sensory organs of macro-fouling larvae, leading to inhibition of settling on the surface.

Adrenergic receptors have been found to play an important role in marine biofouling and as such provide likely targets for prevention of biofouling. For example, for the oyster, studies on the expression and spatial mapping of pediveliger larvae have confirmed that the foot of the animal plays a major sensory role and that sensory nerves terminate at the surface of the foot. In addition, molecular genetics, genomic and immunoblotting studies all independently have confirmed the expression and presence of adrenergic receptors in the oyster larvae. Moreover, adrenergic receptors have been found to be prevalent within organisms and highly conserved across biofouling organisms. For instance, in the case of the Pacific Oyster (*Crassostrea gigas*) genome, genes for 14 different adrenergic receptors have been found. Furthermore, comparative genomic studies have revealed that several marine phyla of benthic and biofouling marine invertebrates show a high degree of adrenergic receptor conservation. For example, the Vase Tunicate (*Ciona intestinalis*) was found to contain 6 adrenergic-like receptors in its genome, all of which align with the *C. gigas* genome. The Sea urchin (*Strongylocentrotus purpuratus*) has been found to possess 66 adrenergric-like receptor sequences, eight of which also aligned with the *C. gigas* genome. Thus, adrenergic receptor binding of a biofouling organism at an aquatic surface is believed to be one route for biofouling prevention.

It should be understood that the mechanism for biofouling prevention by conotoxins present at an aquatic surface is not limited to binding of adrenergic receptors. For example, individual conotoxins present at an aquatic surface can interfere with surface settling of biofouling organisms through binding of dopamine receptors, 5HT receptors, octopamine receptors, and neuropeptide receptors including FF, Y, FMRF, LW-amide, and capa, all of which have been shown to be expressed by macrofouling organisms or any other settlement interference mechanism. Conotoxins present on a surface can prevent settling of biofouling organisms through other routes as well such as, and without limitation, interference with voltage gated channels, ATPases, ion channels and pumps (e.g., calcium, sodium, potassium, etc.), hydrogen channels, and so forth.

In one embodiment, a conotoxin peptide for use as disclosed herein can be from about 10 to about 30 amino acids in length, or from about 10 to about 20 amino acids in some embodiments. In addition, a conotoxin peptide may be identical to a naturally occurring peptide isolated from a cone snail, or can be a derivative or a synthetic thereof.

In one embodiment, a χ-conotoxin can be adhered to an aquatic surface for prevention of biofouling. By way of example, χ-conotoxin peptides as may be adhered to a surface to prevent biofouling can include those described in U.S. Pat. No. 6,794,361 to Lewis, et al.; U.S. Pat. No. 6,849,601 to Lewis, et al.; and U.S. Pat. No. 7,851,444 to Lewis, et al., all of which are incorporated herein by reference thereto. For instance, χ-conotoxin peptides for use as disclosed herein can include one or more of the following sequences:

```
                                              (SEQ ID NO: 1)
Asn Gly Val Cys Cys Gly Tyr Lys Leu Cys His Hyp
Cys (SEQ ID NO: 2)
Val Gly Val Cys Cys Gly Tyr Lys Leu Cys His Hyp
Cys (SEQ ID NO: 3)
Xaa1 Xaa2 Gly Val Cys Cys Gly Tyr Lys Leu Cys His
Pro Cys (SEQ ID NO: 4)
Xaa1 Gly Val Cys Cys Gly Tyr Lys Leu Cys His Hyp
Cys-NH2

(SEQ ID NO: 5)
Xaa1 Gly Val Cys Cys Gly Tyr Lys Leu Cys His Xaa3
Cys (SEQ ID NO: 6)
Xaa1 Gly Val Cys Cys Gly Tyr Lys Leu Cys His Xaa3
Xaa5

(SEQ ID NO: 7)
Xaa1 Gly Val Cys Cys Gly Xaa4 Lys Leu Cys His Xaa3
Cys (SEQ ID NO: 8)
Xaa1 Asn Gly Val Cys Cys Gly Xaa4 Lys Leu Cys His
Xaa3 Cys (SEQ ID NO: 9)
Xaa1 Asn Gly Val Cys Cys Gly Tyr Lys Leu Cys His
Xaa3 Cys (SEQ ID NO: 10)
Xaa1 Gly Val Cys Cys Gly Tyr Lys Leu Cys His Xaa3
Cys-OH (SEQ ID NO: 11)
Xaa1 Gly Val Cys Cys Gly Tyr Lys Leu Cys His Xaa3
Cys-OH (SEQ ID NO: 12)
Xaa1 Gly Val Cys Cys Gly Tyr Lys Leu Cys His Xaa3
Cys
```

In which:
Hyp refers to 4-hydroxy proline,
Xaa1 is pyroglutamate (pGlu) or D-pyroglutamate (Dp-Glu) residue
Xaa2 is Asn or a deletion.
Xaa3 is 4-hydroxyproline,
Xaa4 is 4-methoxy tyrosine,
Xaa5 is D-cysteine and
—OH is a free acid C terminal.
—NH$_2$ is an amine C terminal Of course, conotoxin peptides are not limited to χ-conotoxin peptides and one or more of ω-conotoxin peptides, α-conotoxin peptides, φ-conotoxin peptides, μ-conotoxin peptides, δ-conotoxin peptides, κ-conotoxin peptides, conopressins, conantokin, γ-conotoxin peptides, and/or σ-conotoxin peptides can additionally or alternatively be adhered to a surface for prevention of biofouling. By way of example, and without limitations, conotoxin peptides as encompassed herein can include those described in U.S. Pat. Nos. 8,759, 480; 8,673,856; 8,124,726; 7,387,997; 7,348,400; 7,115, 708; 6,767,896; and 5,591,821, all of which are incorporated herein by reference.

In one embodiment, multiple different conotoxin peptides can be directly or indirectly adhered to the aquatic surface, each of which can be of the same or different conotoxin peptide class as one another. This approach may be useful to provide multi-modal functionality to the aquatic surface. For instance, a plurality of different conotoxin peptides at the aquatic surface can be utilized to prevent biofouling by multiple different organisms in prevention of both microfouling and macrofouling.

A conotoxin peptide encompassed herein includes synthetic and derivative analogs of a natural conotoxin peptide. The term "derivative" as used herein generally refers to a polypeptide that differs from the naturally occurring polypeptide by one or more amino acid deletions, additions, substitutions; or side-chain modifications. The term "synthetic" as utilized herein generally refers to an amino acid residue that is not a naturally occurring residue as well as to a synthetic analog of an entire polypeptide oligomer. All such derivatives and synthetics exhibit the ability to prevent biofouling of a surface to which the conotoxin peptide is adhered. Amino acid substitutions are typically of single residues, but may be of multiple residues, either clustered or dispersed.

Substitutions encompass amino acid alterations in which an amino acid is replaced with a different naturally-occurring or a non-conventional amino acid residue. Such substitutions may be classified as "conservative", in which case an amino acid residue contained in a peptide is replaced with another naturally-occurring amino acid of similar character either in relation to polarity, side chain functionality or size, for example Ser↔Thr↔Pro↔Hyp↔Gly↔Ala, Val↔Ile↔Leu, His↔Lys↔Arg, Asn↔Gln↔Asp↔Glu or Phe↔Trp↔Tyr. It is to be understood that non-conventional amino acids may also be suitable replacements for naturally occurring amino acids. For example Lys residues may be substituted by ornithine, homoarginine, nor-Lys, N-methyl-Lys, N,N-dimethyl-Lys and N,N,N-trimethyl-Lys. Lys residues can also be replaced with synthetic basic amino acids including, but not limited to, N-1-(2-pyrazolinyl)-Arg, 2-(4-piperinyl)-Gly, 2-(4-piperinyl)-Ala, 2-[3-(2S)pyrrolininyl]-Gly and 2-[3-(2S)pyrolininyl]-Ala. Tyr residues may be substituted with 4-methoxy tyrosine (MeY), meta-Tyr, ortho-Tyr, nor-Tyr, $^{125}$I-Tyr, mono-halo-Tyr, di-halo-Tyr, O-sulpho-Tyr, O-phospho-Tyr, and nitro-Tyr. Tyr residues may also be substituted with the 3-hydroxyl or 2-hydroxyl isomers, (meta-Tyr or ortho-Tyr, respectively) and corresponding O-sulpho- and O-phospho derivatives. Tyr residues can also be replaced with synthetic hydroxyl containing amino acids including, but not limited to 4-hydroxymethyl-Phe, 4-hydroxyphenyl-Gly, 2,6-dimethyl-Tyr and 5-amino-Tyr. Aliphatic amino acids may be substituted by synthetic derivatives bearing non-natural aliphatic branched or linear side chains $C_nH_{2n+2}$ up to and including n=8. Substitutions are generally restricted to conservative substitutions.

Side chain modification can be carried out in one embodiment to provide functionality for binding a peptide to an aquatic surface or a component of a coating composition. Examples of side chain modifications contemplated by the present disclosure include modifications of amino groups such as by reductive alkylation by reaction with an aldehyde followed by reduction with NaBH$_4$; amidation with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$; and N-acetylation. In one embodiment, side chain modification can be carried out at a terminal amino acid of the peptide to provide functionality for bonding the peptide to a surface.

By way of example and without limitation, a guanidine group of arginine residues may be modified by the formation of heterocyclic condensation products with reagents such as 2,3-butanedione, phenylglyoxal and glyoxal; a carboxyl group may be modified by carbodiimide activation via O-acylisourea formation followed by subsequent derivatisation, for example, to a corresponding amide; acidic amino acids may be substituted with tetrazolyl derivatives of glycine and alanine; the tyrosine residue may be altered, for example by methoxylation at the 4-position; tyrosine may also be altered by nitration with tetranitromethane to form a 3-nitrotyrosine derivative; modification of the imidazole ring of a histidine residue may be accomplished by alkylation with iodoacetic acid derivatives or N-carbethoxylation with diethylpyrocarbonate; proline residues may be modified by, for example, hydroxylation in the 4-position.

Other derivatives contemplated include glycosylation variants. For instance, Ser, Thr and Hyp residues may be modified to contain an O-glycan, while Asn and Gln residues can be modified to form a N-glycan. In accordance with the present disclosure, the term "glycan" generally refers to an N-, S- or O-linked mono-, di-, tri, poly- or oligosaccharide that can be attached to any hydroxy, amino or thiol group of natural of modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNac), D-fucose or D-arabinose. These saccharides may be structurally modified e.g., with one or more O-sulphate, O-phosphate, O-acetyl or acidic groups such as sialic acid, including combinations thereof. The glycan may also include similar polyhydroxyl groups, such as D-penicillamine 2,5 and halogenated derivatives thereof or polypropylene glycol derivatives. The glycosidic linkage is beta and 1-4 or 1-3, preferably 1-3. The linkage between the glycan and the amino acid may be alpha or beta, preferably alpha and is 1.

The conotoxin peptide can also be labeled for instance for use to establish binding assays to identify new molecules that act in a similar fashion. For example, a labeled peptide ligand could have tritium included or may have radioactive iodine, a fluorochrome, a quenching agent, or similar attached through a Tyr or other appropriate residue.

A conotoxin peptide may be prepared using standard peptide synthetic methods followed by oxidative disulfide bond formation. For example, a peptide may be synthesized by solid phase methodology using BOC chemistry, as described by Schnoltzer et al. (1992). Following deprotection and cleavage from the solid support the reduced peptides can be purified using preparative chromatography. The purified reduced peptides can be oxidized in buffered systems, and the oxidized peptides can be purified using preparative chromatography. Methods for synthesizing conotoxins have been described in U.S. Pat. No. 5,051,403 to Miljanich, et al., which is incorporated herein by reference The conotoxin peptide may also be prepared using recombinant DNA technology. A nucleotide sequence encoding the desired peptide sequence may be inserted into a suitable vector and protein expressed in an appropriate expression system. In some instances, further chemical modification of the expressed peptide may be appropriate, for example C-terminal amidation and conversion of an N-terminal glutamate residue to pyroglutamate residue. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

One or more conotoxins can be directly or indirectly adhered to an aquatic surface in order to impart the anti-biofouling effects of the conotoxins to the surface. As utilized herein, the term "directly adhered" generally refers to a conotoxin peptide that is covalently or non-covalently (e.g., electrostatically) bonded to the aquatic surface itself. A directly adhered conotoxin peptide can be bonded to the surface via reaction between a reactive functionality of the peptide (generally a terminal reactive functionality at the C-terminus or the N-terminus of the peptide) and a reactive functionality of the surface. Alternatively, a linking agent can be utilized to directly bond the conotoxin peptide to the surface. For instance, a multifunctional linking agent, which can be monomeric or polymeric, can serve as an anchor between the surface and one or more conotoxin peptides.

As utilized herein, the term "indirectly adhered" generally refers to a conotoxin peptide that is a component of a coating composition that can be applied to the aquatic surface. The conotoxin peptide can be merely blended with the other components of the coating composition or can be bonded to a component of the coating composition. For instance, the conotoxin peptide can be bonded to a polymeric component of the coating composition, either via direct covalent or non-covalent bonding between a reactive functionality of the component and a reactive functionality of the peptide or via a linking agent, which can be monomeric or polymeric, and can serve to link the conotoxin peptide to the component of the coating composition.

As utilized herein the terms "coating composition" and "coating" are synonymous and generally refer to any temporary, semi-permanent or permanent layer or covering. Examples of coatings include polishes, surface cleaners, caulks, adhesives, finishes, paints, waxes, and polymerizable compositions (including phenolic resins, silicone polymers, chlorinated rubbers, coal tar and epoxy combinations, epoxy resin, polyamide resins, vinyl resins, elastomers, acrylate polymers, fluoropolymers, polyesters and polyurethanes, latex). Silicone resins, silicone polymers (e.g. room temperature vulcanizing (RTV) polymers) and silicone heat cured rubbers are other examples of coatings for an aquatic surface. A commercial marine paint vehicle that is suitable for the practice of this disclosure is Amerlock 698, a product of Ameron International, Pasadena, Calif. Comparable marine paint vehicles are also available from Jotan, A S, Sandefjord, Norway. Marine coating compositions available from Ztech Technologies of Redmond, Mich. can also be utilized in conjunction with conotoxin peptides as described herein.

When bound to a substrate (either directly to the aquatic surface or indirectly to a component of a surface coating), it is necessary to ensure that the conotoxin peptide maintains activity so as to successfully interact with the sensory apparatus of the settling organism and prevent biofouling. This can be accomplished by binding the conotoxin peptide to a substrate in an orientation that maintains desired activity. In one embodiment, this can be accomplished by binding the conotoxin peptide via the N-terminus of the conotoxin peptide.

In one embodiment, activity of a bonded conotoxin peptide can be maintained by synthesizing a peptidic or non-peptidic linking agent that bonds to the formed conotoxin peptide, e.g., via the N-terminus of the peptide, and bonds to a substrate via a suitable functionality as determined by the chemistry of the substrate surface. By way of example, a linking agent can be a modified glycyl chain including a COO⁻ terminus for binding a conotoxin peptide, two or more glycyl units in a polymeric chain, and a second terminus for binding a substrate.

The glycyl chain can be of any suitable length. In one embodiment a relatively long glycyl chain (e.g., about 50 mer chain or greater) can be utilized. A shorter chain can be utilized in other embodiments, e.g., from about a 5 to about a 10 mer chain, or about a 7 mer glycl chain in some embodiments. The glycyl chain can be modified such that the amino terminus bears a residue that can interact and bind with the substrate. For example, a 7 mer glycyl chain can be modified to form linking agent having a structure of:

(SEQ ID NO: 14)
HOOC-GLY-GLY-GLY-GLY-GLY-GLY-GLY-X where X can include a functional group capable of binding to a substrate surface (e.g., amine, acid, etc.). In one embodiment, the X group can be a linolenic acid group that can interact and bind to the substrate.

The conotoxin peptide to be bonded to a substrate can be bonded to the linking agent (e.g., a modified glycyl chain) following which the peptide can be bonded to the substrate via the linking agent. For instance, following successful secondary structure formation, including folding and disulfide bridge formation of a synthetic bioactive conotoxin peptide, the conotoxin peptide can be attached to a linking agent (e.g., a modified glycyl chain) using a suitable chemistry to form a complete intact molecule, (e.g., HOOC-conotoxin peptide-modified glycyl chain terminated with a functional group for bonding a substrate).

In one embodiment, linking chemistry for binding a conotoxin peptide to linking agent can incorporate "click chemistry." Click chemistry has been introduced as a way of categorizing organic reactions that are highly efficient, modular and selective, and occur with simple work-up procedures. By using the efficient click reaction, different architectures of macromolecules such as dendrimers, dendronized linear polymers, hydrogels, supra-polymers and novel conjugated polymers can be created. Click chemistry strategy has also been implemented for the preparation of segmented copolymers of monomers polymerizable by different mechanisms. Peptide modification by use of click chemistry has been described, for instance in International Patent Application Publication WO 2011/045316 to Carell and U.S. Patent Application Publication No. 2014/0249296 to Ploegh, et al., which is incorporated herein by reference.

Following bonding of the conotoxin peptide to the linking agent, functionality of the linking agent can be utilized to bind the conotoxin peptide to the substrate, e.g., via an acid/amine reaction to form an amide bond between the substrate and the linking agent. Thus, the conotoxin peptide can be bonded to a substrate (either the aquatic surface itself or a component of a coating composition) via the linking agent.

Any suitable reactive functionality can be utilized to directly or indirectly adhere a conotoxin peptide to an aquatic surface such as, and without limitation, thiol, primary amine, secondary amine, nitrile, aldehyde, imidazole, azide, halide, polyhexamethylene dithiocarbonate, hydrogen, hydroxyl, carboxylic acid, carboxylic ester or carboxamide. The particular functionality can vary, generally depending upon the nature of the substrate to which the conotoxin peptide is to be bonded. It is recognized that aquatic surfaces can be comprised of many different materials, e.g., metal, wood, concrete, plastic, etc., any of which can be modified to include a conotoxin peptide directly bonded thereto. Likewise, with regard to indirect adherence of the conotoxin peptide to the surface, while the conotoxin peptide can in one embodiment be bonded to an organic polymeric component of a coating composition, this is not a requirement of the disclosure, and any component of a coating composition can be utilized to indirectly adhere a conotoxin peptide to an aquatic surface. Thus, any suitable reactivity can be utilized in forming a covalent or non-covalent bond between a conotoxin peptide and a substrate.

A substrate (i.e., an aquatic surface or a component of a coating) can already include suitable functionality for bonding to a conotoxin peptide. Alternatively, a substrate can be pretreated to include the reactive functionality. For instance, a substrate can be chemically processed via, e.g., oxidation with strong acid, ozone treatment, chemisorption, or flame treatment. In one embodiment, a substrate can be functionalized by use of radiation treatment, such as glow discharge, corona discharge, photo activation (e.g., UV treatment), laser, ion implantation, ion bombardment, electron beam, γ irradiation, plasma treatment, and so forth.

Alkali hydrolysis, covalent immobilization, and the wet chemical methods are examples of substrate modification methods as may be utilized to directly bond a conotoxin peptide to the substrate. For instance, according to an alkali hydrolysis method, a strong nucleophile (e.g., hydroxide ion) is utilized to encourage hydrolysis of a substrate and results in the formation of carboxyl and hydroxyl functionalities which can form bonds with reactive functionality of the peptides.

As stated, a linking agent can be utilized to bond a conotoxin peptide to a substrate, i.e., either an aquatic surface or a component of a coating composition. A linking agent can be monomeric or polymeric. By way of example, a linking agent can include but is not limited to polyfunctional epoxides including di-epoxides, polyisocyanates including diisocyanates, polyhydric alcohols, carbodiimides, diamines, diaminoalkanes, polyfunctional carboxylic acids including dicarboxylic acids, diacid halides, and so forth.

Specific examples of polyfunctional carboxylic acid linking agents can include, without limitation, isophthalic acid, terephthalic acid, phthalic acid, 1,2-di(p-carboxyphenyl)ethane, 4,4'-dicarboxydiphenyl ether, 4,4'-bisbenzoic acid, 1,4- or 1,5-naphthalene dicarboxylic acids, decahydronaphthalene dicarboxylic acids, norbornene dicarboxylic acids, bicyclooctane dicarboxylic acids, 1,4-cyclohexanedicarboxylic acid (both cis and trans), 1,4-hexylenedicarboxylic acid, adipic acid, azelaic acid, dicarboxyl dodecanoic acid, succinic acid, maleic acid, glutaric acid, suberic acid, azelaic acid, stearic acid, and sebacic acid. The corresponding dicarboxylic acid derivatives, such as carboxylic acid diesters having from 1 to 4 carbon atoms in the alcohol radical, carboxylic acid anhydrides or carboxylic acid halides may also be utilized.

Exemplary diols useful as linking agents can include, without limitation, aliphatic diols such as ethylene glycol, 1,2-propylene glycol, 1,3-propylene glycol, tetra ethylene glycol, 2,2-dimethyl-1,3-propane diol, 2-ethyl-2-methyl-1,3-propane diol, 1,4-butane diol, 1,4-but-2-ene diol, 1,3-1,5-pentane diol, 1,5-pentane diol, dipropylene glycol, 2-methyl-1,5-pentane diol, and the like. Aromatic diols can also be utilized such as, without limitation, hydroquinone, catechol, resorcinol, methylhydroquinone, chlorohydroquinone, bisphenol A, tetrachlorobisphenol A, phenolphthalein, and the like. Exemplary cycloaliphatic diols as may be used include a cycloaliphatic moiety, for example 1,6-hexane diol, dimethanol decalin, dimethanol bicyclooctane, 1,4-cyclohexane dimethanol (including its cis- and trans-isomers), triethylene glycol, 1,10-decanediol, and the like.

Exemplary diamines that may be utilized as linking agents can include, without limitation, isophorone-diamine, ethylenediamine, 1,2-, 1,3-propylene-diamine, N-methyl-1,3-propylene-diamine, N,N'-dimethyl-ethylene-diamine, and aromatic diamines, such as, for example, 2,4- and 2,6-toluoylene-diamine, 3,5-diethyl-2,4- and/or -2,6-toluoylene-diamine, and primary ortho-di-, tri- and/or tetra-alkyl-substituted 4,4'-diaminodiphenyl-methanes, (cyclo)aliphatic diamines, such as, for example, isophorone-diamine, ethylenediamine, 1,2-, 1,3-propylene-diamine, N-methyl-1,3-propylene-diamine, N,N'-dimethyl-ethylene-diamine, and aromatic diamines, such as, for example, 2,4- and 2,6-toluoylene-diamine, 3,5-diethyl-2,4- and/or -2,6-toluoylene-diamine, and primary ortho-di-, tri- and/or tetra-alkyl-substituted 4,4'-diaminodiphenyl-methanes.

As with bonding to the substrate without any linking agent present, a substrate can include suitable reactive functionality for bond formation with a linking agent or can be pre-treated to include suitable functionality. For example, a substrate may first be exposed to a plasma to produce active sites on the substrate. Following, the active sites can be reacted with a multifunctional molecule to provide a surface-bound linking agent on the substrate surface. The surface-bound linking agent can then optionally be reacted with one or more additional multifunctional molecules to form an extended linking agent chain. Finally, conotoxin peptides may be immobilized on the substrate by reacting them with reactive functionality of the linking agent. Alternatively, a conotoxin peptide can first be reacted with the linking agent and following, the linking agent/peptide complex can be bonded to the substrate.

In one embodiment, a polyethylene glycol linking agent can be utilized to adhere a conotoxin peptide to an aquatic surface. For example, a polyethylene glycol can be activated with an oxycarbonyl-N-dicarboximide functional group that can be attached under aqueous, basic conditions by a urethane linkage to the amine group of a conotoxin peptide and to a substrate surface as described in U.S. Pat. No. 5,122,614 to Zalipsky, which is incorporated herein by reference. A polyethylene glycol linking agent can be utilized in one embodiment to directly bond a conotoxin peptide to a transparent aquatic surface so as to provide a transparent anti-fouling surface. It should be understood, however, that other adherence mechanisms are encompassed herein for forming a transparent anti-fouling aquatic surface.

In one embodiment, a polymeric linking agent can include a stearic acid component. For instance, an amine group of a conotoxin peptide can be crosslinked with a carboxylic group of stearic acid by use of 1-ethyl-3-(3-dimethylaminopropyl) carbodiimide (EDC) as linker. Carbodiimide chemistry can also be utilized to bond the stearic acid to a substrate. Alternatively, a different chemistry can be utilized to bond the stearic acid linking agent to the substrate as is used to bond the linking agent to a conotoxin peptide. The preferred bonding chemistry for bonding the linking agent to the substrate can generally depend upon the nature of the substrate.

In another exemplary embodiment, a polyfunctional ethylene glycol linking agent can be utilized as described by Zhao, et al. (Journal of Biomedical Materials Research A, January 2012, Vol. 100A, Iss. 1). Briefly, a hetero-bifunctional tetra(ethylene glycol) molecule with silane and azide termini can be synthesized, and this molecule can be used to prepare azide-derivatized surface in one step. The resulting surface can be available for conjugation with alkyne-containing peptide, which can proceed at low temperature and in aqueous solution. A high density of peptide on the surface can be achieved due to concise overall procedure and the highly efficient conjugation reaction.

A coating composition as may be utilized in conjunction with a conotoxin peptide can generally include a polymer base. The term "polymer base" as utilized herein generally refers to any polymer or mixtures of polymers suitable for admixing with and/or bonding to a conotoxin peptide and that may be used for the coating of an aquatic surface. Paint, for example, may comprise a mixture of a polymeric base and a suitable solvent or suspension medium (e.g., water). The paint may be an ablative paint wherein the immediate outer surface of the applied paint coating may be removed by frictional forces as a hull moves through water. The ablation will contribute to the removal of any colonizing organisms, as well as maintain the conotoxin peptide at the surface. A polymer base may, for example, encompass a latex base, a polymeric epoxy base, or the like.

A variety of synthetic and natural polymers can be included in a polymer base. Examples of suitable polymers include, without limitation, polyester resins, vinyl ester resins, vinyl acetate resins, vinyl chloride resins, polyurethane based resins, chlorinated rubber resins, chlorinated polyethylene resins, chlorinated polypropylene resins, styrene-butadiene resins, epoxy resins, phenol resins, synthetic rubbers, silicone rubbers, silicone resin, petroleum resins, oil and fat resins, rosin ester resins, and/or rosin soaps. Polyester based resins include those formed from unsaturated acids and anhydrides, saturated acids and anhydrides, glycols, and glycol monomers. A polymer base can include blends of polymers, for instance a blend of natural polymeric material (e.g., rosin) and synthetic materials (e.g., vinyl chloride-vinyl acetate co-polymers). Vinyl resins, alkyd resins, epoxy resins, acrylic resins, vinyl acrylic copolymer resins, vinyl esters (e.g., vinyl esters of $C_{2-20}$ linear or branched alkanoic, alkenoic, alkyldienoic acids) and combinations thereof are encompassed herein.

In one embodiment, a polymer base can include one or more acrylic resins (e.g., polyester acrylic resins, epoxy acrylic resins, polyether acrylic resins, vinyl acrylic resins, styrene/acrylic copolymer resins, urethane acrylic resins, fluoroalkyl (meth)acrylate/silyl (meth)acrylate/alkyl (meth) acrylate terpolymers (e.g., as described in U.S. Pat. No. 6,767,978, to Aubart, et al., which is incorporated herein by reference), acrylic emulsion resins and polyol acrylic resins). Copolymers of vinyl chloride, vinyl isobutyl ether, carboxylic acid functional polymers and combinations thereof are also encompassed including vinyl chloride-vinyl acetate copolymers, vinyl chloride-vinyl isobutyl ether copolymers, etc. Copolymers can include, without limitation, copolymers of vinyl ethers such as vinyl methyl ether, vinyl ethyl ether, vinyl propyl ether, vinyl ethylbutyl ether, vinyl hexyl ether, vinyl 2-ethylhexyl ether, and vinyl cyclohexyl ether. Copolymers of vinyl chlorides and vinyl isobutyl ethers include those sold by BASF under the trade name Laroflex®.

A polymer base may include one or more natural rosins. For example, a rosin can be a gum rosin, wood rosin of grade B, C, D, E, F, FF, G, H, I, J, K, L, M, N, W-G, W-W (as defined by the ASTM D509 standard), virgin rosin, hard rosin, yellow dip rosin, NF wood rosin, tail oil rosin, colophony, colophonium, single constituent of natural rosin (e.g., abietic acid, abietinic acid, sylvic acid, dihydroabietic acid, tetrahydroabietic acid, dehydroabietic acid, neoabietic acid, pimaric acid, laevopimaric acid, isopimaric acid, sandaracopimaric acid, palustric acid, dextro-pimaric acid, isodextro-pimaric acid, dextro-pimarinal, isodextro-pimarinal, xanthoperol, tatarol, podocarpic acid, phyllocladen, sugiol, ferruginol, himokiol, manool, manoyloxide, ketomanoyloxide, cativinic acid, eperuanic acid and all other rosin components based on the diterpene skeleton of abietic acid) and combinations thereof.

In various embodiments, a coating composition can include a diluent. A diluent can include, for example, and without limitation, alcohols, aliphatic, cycloaliphatic and aromatic hydrocarbons, ketones, ether alcohols, esters, chlorinated hydrocarbons and combinations thereof. Typically, a diluent may function as a solvent for a component (e.g., a resin) of the composition. For instance, a diluent can include methanol, ethanol, propanol, isopropanol, butanol, isobutanol, benzyl alcohol, white spirit, cyclohexane, toluene, xylene, methyl ethyl ketone, acetone, methyl isobutyl ketone, methyl isoamyl ketone, diacetone alcohol, cyclohexanone, 2-butoxyethanol, propylene glycol monomethyl ether, butyl diglycol, methoxypropyl acetate, n-butyl acetate, 2-ethoxyethyl acetate, methylene chloride, tetrachloroethane, trichloroethylene and combinations thereof.

Typically, a diluent will evaporate once the coating composition is applied to the aquatic surface. As such, the dried and/or cured coating can have a minimal concentration of diluents in the coating.

Additives as are generally known in the art can be included in a coating composition. Additives can include, for example, one or more of pigments, fillers, extenders, swelling agents, wetting agents, biocides and combinations thereof. Pigments, for example, can be organic or inorganic pigments. Typical pigments for use in coatings can include phthalo blue, hansa yellow, ochres, umbers, Quinacridone Red, Pigment Red, Phthalocyanine Blue, Phthalocyanine Green, Perylene Red, carbon black, rutile and anatase titanium dioxides, lithopone, zinc sulfide, lead titanate, antimony oxide, zirconium oxide, barium sulfide, white lead, zinc oxide, leaded zinc oxide, red iron oxide, brown oxide, aluminum powder, vapor-deposited aluminum powder, alumina powder, nickel powder, copper powder, brass powder, chromium powder, nacreous pearl mica powder and nacreous colored pearl mica powder and combinations thereof.

A coating composition can include one or more fillers. Fillers generally include those additives having a fine particle size, are dispersible in the solvent media of the coating composition and do not settle once dispersed. Exemplary fillers include calcium carbonate, iron oxide, kaolin, clay, titanium dioxide, alumina trihydrate, pyrophyllite, quartz, silica, fumed silicas, precipitated silicas, silicates, barium sulfate, antimony oxide, mica, calcium sulfate, magnesium hydroxide, feldspar, nepheline syenite, carbon black filler, titanates, talc, gypsum, silex, wollastonite, bagasse, coconut hull/fiber, cork, corn, cotton-based, filsonite, nutshell flour, rice hull, sisal/hemp, soybean, starch wood flour and combinations thereof.

A coating composition can optionally include one or more wetting agents. Wetting agents are substances that can reduce the surface tension of a liquid and cause the liquid to spread across or penetrate more easily the surface of a solid. Exemplary wetting agents as may be included in a coating composition can include, without limitation, a solution of a salt of unsaturated polyamine amides and lower molecular acid polymers, sodium polyphosphate, aryl or alkyl phosphates, salts of low molecular weight poly(acrylic acid), salts of sulfonated polyethylene, salts of poly (vinyl-phosphonic acid), salts of poly(maleic acid), salts of copolymers of maleic acid with olefins, and combinations thereof.

Following formation, a coating composition can be applied to an aquatic surface. For instance, a coating composition can be brushed or sprayed on a surface or applied as a dip coating, for instance in application on a surface such as a rope. Any suitable application method is encompassed herein. In one embodiment, a composition may also be used to coat the exterior surfaces of cultivated mollusks such as oysters or mussels, thereby limiting the growth thereon of organisms which might slow the growth rate of the farmed shellfish either directly by overgrowing, or restricting the flow of clean water.

The present disclosure may be better understood with reference to the example set forth below.

Example

Cyprid larval settlement and attachment was examined in solutions of various concentrations of the χ-conotoxin peptide:

pGlu Gly Val Cys Cys Gly Tyr Lys Leu Cys His
Hyp Cys-NH$_2$                    (SEQ ID NO: 13)

Solutions included 5 mg/ml of the peptide dissolved in a solution containing dimethylsulfoxide (DMSO) 3 mg/ml of the peptide dissolved in a solution containing DMSO, 1 mg/ml of the peptide dissolved in a solution containing DMSO, 0.1 mg/ml of the peptide dissolved in a solution containing DMSO, 0.01 mg/ml of the peptide dissolved in a solution containing.

The solution was found to cause apoptosis in oyster hemocytes at 5 mg/ML concentration.

3 day old cyprid attachment studies revealed that the soluble peptide inhibited cyprid settlement at 3 mg/mL and promoted settlement at 1 mg/mL (FIG. 1). The tested surface was a cover glass placed in a standard petri dish. On the FIGURE, dish, cont, and DMSO are negative controls. The categories included dish—measurement of settlement by cyprids on the surface of the plastic petri dish; cont—negative control measurement of settlement by cyprids on the cover glass; DMSO—measurement of settlement by cyprids in a solution containing dimethylsulfoxide only at the same final concentration in the dish as the soluble treatments.

Without wishing to be bound to any particular theory, it is believed that SEQ ID NO: 13 induced settlement at low concentration due to the fact that the cyprid's adrenergic receptors were stimulated by the peptide. This is believed to be a threshold effect, which implies that there are a minimum number of receptors that are needed to bind to the ligand to elicit a behavior response, which in this case is stimulatory. At the higher concentration, the effect is inhibitory to settlement. Since these effects were noted with the soluble peptide, this anti-fouling effect of the peptide occurs prior to cyprid's surface exploration.

While certain representative embodiments and details have been shown for the purpose of illustrating the subject invention, it will be apparent to those skilled in this art that various changes and modifications may be made therein without departing from the scope of the subject invention.

What is claimed is:

1. A substrate comprising a surface, a polymeric linking agent bonded to the surface, and a a conotoxin peptide bonded to the polymeric linking agent such that the polymeric linking agent is between the surface and the conotoxin peptide.

2. The substrate of claim 1, wherein the conotoxin peptide is a χ-conotoxin peptide.

3. The substrate of claim 1, wherein the conotoxin peptide comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

4. The substrate of claim 1, wherein the conotoxin peptide is covalently bonded to the linking agent.

5. The substrate of claim 1, wherein the surface comprises the conotoxin peptide in an amount of about $10^{14}$ peptides per square centimeter or greater.

6. The substrate of claim 1, wherein the conotoxin peptide is bonded to the polymeric linking agent via an N-terminus of the conotoxin peptide.

7. The substrate of claim 1, wherein the polymeric linking agent is a peptidic polymeric linking agent.

8. The substrate of claim 7, wherein the peptidic polymeric linking agent comprises a glycyl chain.

9. The substrate of claim 1, wherein the polymeric linking agent is bonded to the surface via a reaction product of a terminal functionality of the polymeric linking agent, the terminal functionality being selected from the group consisting of thiol, primary amine, secondary amine, nitrile, aldehyde, imidazole, azide, halide, polyhexamethylene dithiocarbonate, hydrogen, hydroxyl, carboxylic acid, carboxylic ester and carboxamide.

10. The substrate of claim 9, wherein the polymeric linking agent is bonded to the surface via a the reaction product of the terminal functionality of the polymeric linking agent with a reactive functionality of the surface.

11. The substrate of claim 10, wherein the reactive functionality of the surface is a product of a substrate pretreatment process.

12. The substrate of claim 9, wherein the reaction product is a product of a reaction between an azide and an alkyne.

13. The substrate of claim 1, wherein the linking agent is selected from the group consisting of a polyfunctional epoxide, a polyisocyanate, a polyhydric alcohol, a carbodiimide, a diamine, a diaminoalkane, and a polyfunctional carboxylic acid.

14. The substrate of claim 1, wherein the polymeric linking agent is bonded to the surface via a surface-bound multifunctional molecule.

15. The substrate of claim 1, wherein the surface comprises metal, wood, concrete, glass, or an organic polymer.

16. A coating composition comprising the substrate of claim 1.

17. The coating composition of claim 16, wherein the coating composition is a marine paint.

* * * * *